(12) United States Patent
Fong et al.

(10) Patent No.: US 7,090,845 B2
(45) Date of Patent: Aug. 15, 2006

(54) DIAGNOSIS AND TREATMENT OF HEPATIC DISORDERS

(75) Inventors: Sherman Fong, Alameda, CA (US); Kenneth J. Hillan, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/213,539

(22) Filed: Aug. 6, 2002

(65) Prior Publication Data

US 2003/0003108 A1 Jan. 2, 2003

Related U.S. Application Data

(63) Continuation of application No. 09/310,247, filed on May 12, 1999, now abandoned.

(60) Provisional application No. 60/085,326, filed on May 13, 1998.

(51) Int. Cl.
*A61K 39/395* (2006.01)
*A61K 39/40* (2006.01)
*C12N 7/00* (2006.01)
*C07H 21/02* (2006.01)

(52) U.S. Cl. .............. 424/144.1; 424/134.1; 424/152.1; 435/235.1; 536/23.1

(58) Field of Classification Search .............. None
See application file for complete search history.

(56) References Cited

U.S. PATENT DOCUMENTS

| 5,284,931 | A | * | 2/1994 | Springer et al. | ......... 424/139.1 |
| 5,962,422 | A | | 10/1999 | Nagy et al. | |
| 5,968,775 | A | * | 10/1999 | Houghton et al. | ......... 435/69.3 |
| 6,020,347 | A | | 2/2000 | DeLaszlo et al. | |
| 6,037,324 | A | | 3/2000 | Schwender et al. | |
| 6,551,593 | B1 | * | 4/2003 | Ringler et al. | ........... 424/143.1 |

FOREIGN PATENT DOCUMENTS

| WO | WO 96/24673 | 8/1996 |
| WO | WO 97/25351 | 7/1997 |

OTHER PUBLICATIONS

Hu, K.Q. "up-regulation of intercellular adhesion molecule 1 transcription by hepatitis B virus X protein" Proc. Natl. Acad. Sci. (1992) vol. 89, pp. 11441-11445.*

Lalor. P.F. "Vascular adhesion protein-1 mediates adhesion and transmigration of lymphocytes on human hepatic endothelial cells" J. Immunol. (2002) vol. 169, No. 2, pp. 983-992.*

Nolte. D. "Attenuation of Leukocyte Sequestration by Selective Blockade of PECAM-1 or VCAM-1 in Murine Endotoximia" Europ. Surg. Res. (2004) Vol. 36, pp. 331-337.* http://www.merck.com/mrkshared/mmanual/section4/chapter41/41a.jsp.*

Grant, A.J. "MAdCAM-1 Expressed in Chronic Inflammatory Liver Disease Supports Mucosal Lymphocyte Adhesion to Hepatic Endothelium" Hepatology (2001) 33, 5, 1065-1072.*

Berlin et al., "α4 integrins mediate lymphocyte attachment and rolling under physiologic flow" *Cell* 80(3) :413-422 (Feb. 10, 1995).

Berlin et al., "α4β7 integrin mediates lymphocyte binding to the mucosal vascular addressin MAdCAM-1" *Cell* 74(1) : 185-195 (Jul. 16, 1993).

Briskin et al., "Human mucosal addressin cell adhesion molecule-1 is preferentially expressed in intestinal tract and associated lymphoid tissue" *American Journal of Pathology* 151(1) :97-110 (Jul. 1997).

Briskin et al., "MAdCAM-1 has homology to immunoglobulin and mucin-like adhesion receptors and to IgA1" *Nature* 363(6428) :461-464 (Jun. 3, 1993).

Erle et al., "Complete amino acid sequence of an integrin β subunit (β7) identified in leukocytes" *Journal of Biological Chemistry* 266(17) :11009-11016 (Jun. 15, 1991).

(Continued)

*Primary Examiner*—James Housel
*Assistant Examiner*—Timothy Brown
(74) *Attorney, Agent, or Firm*—Merchant & Gould P.C.

(57) ABSTRACT

The present invention encompasses methods and compositions useful in diagnosing and treating hepatic disorders, especially those characterized by inflammation. The method comprises administration of an agent which prevents the interaction of MAdCAM with a MAdCAM binding partner or ligand. These compositions are useful in treating diseases or disorders involving α4β7/MAdCAM blockade, as well as inhibiting a primary event in the inflammatory response such as blocking interactions between intercellular adhesion molecules and their ligands. Disorders treatable using the methods disclosed herein include infections, especially viral infections, iatrogenic disorders, cholestatic disorders, hereditary disorders, sarcoidosis, organ transplant, and the like. The diagnostic methods of the invention can be employed to detect the presence of a disorder or to monitor the course of therapy used to treat the disorder.

26 Claims, 2 Drawing Sheets

OTHER PUBLICATIONS

Gurish et al., "Expression of murine $\beta_7$, $\alpha_4$, and $\beta_1$ integrin genes by rodent mast cells" *Journal of Immunology* 149(6) : 1964-1972 (Sep. 15, 1992).

Hanninen et al., "Vascular addressins are induced on islet vessels during insulitis in nonobese diabetic mice and are involved in lymphoid cell binding to islet endothelium" *Journal of Clinical Investigation* 92(5) :2509-2515 (Nov. 1993).

*Harrison's Priciple of Internal Medicine*, 14 edition pp. 1736 (1998),

Hesterberg et al., "Rapid resolution of chronic colitis in the cottom-top tamarin with an antibody to a gut-homing integrin $\alpha 4\beta 7$" *Gastroenterology* 111(5) :1373-1380 (Nov. 1996).

Hillan et al., "Hepatic expression of the mucosal vascular addressin, MAdCAM-1, in hepatitis C" *Modern Pathology* (Abstract #956 from the Annual Meeting of the United States and Canadian Academy of Pathology held in San Francisco on Mar. 20-26, 1999) 12(1) :163A (Jan. 1999).

Jackson et al., "Potent $\alpha 4\beta 1$ Peptide Antagonists as Anti-Inflammatory Agents" *Journal of Medicinal Chemistry* 40(21) :3359-3368 (Oct. 10, 1997).

Kilger and Holzmann, "Molecular analysis of the physiological and pathophysiological role of $\alpha_4$-integrins" *Journal of Molecular Medicine* 73(7) :347-354 (Jul. 1995).

Kilshaw and Murant, "Expression and regulation of $\beta_7(\beta_p)$ integrins on mouse lymphocytes: relevance to the mucosal immune system" *European Journal of Immunology* 21(10) :2591-2597 (Oct. 1991).

Kraal et al., "Expression of the mucosal vascular addressin, MAdCAM-1, on sinus-lining cells in the spleen" *American Journal of Pathology* 147(3) :763-771 (Sep. 1995).

Kwan, M., "Examination of serum MAdCAM-1 levels in inflammatory bowel disease in an IL-10 receptor knockout model and its correlation to disease" (Abstract #73. Presented at the 10th Annual UC Davis Undergraduate Research Conference on Apr. 24, 1999).

Lazarovits et al., "Lymphocyte activation antigens. I. A monoclonal antibody, anti-Act I, defines a new late lymphocyte activation antigen" *Journal of Immunology* 133(4) : 1857-1862 (Oct. 1984).

Madara et al., "Characterization of spontaneous colitis in cotton-top tamarins (Saguinus oedipus) and its response to sulfasalazine" *Gastroenterology* 88(1 Pt 1) :13-19 (Jan. 1985).

Picarella et al., "Monoclonal antibodies specific for $\beta_7$ integrin and mucosal addressin cell adhesion molecule-1 (MAdCAM-1) reduce inflammation in the colon of scid mice reconstituted with CD45RBhigh CD4+ T cells" *Journal of Immunology* 158(5) :2099-2106 (Mar. 1, 1997).

Podolsky et al., "Attenuation of colitis in the cotton-top tamarin by anti-$\alpha 4$ integrin monoclonal antibody" *Journal of Clinical Investigation* 92(1) :372-380 (Jul. 1993).

Schweighoffer et al., "Selective expression of integrin $\alpha 4\beta 7$ on a subset of human CD4$^+$memory T cells with Hallmarks of gut-trophism" *Journal of Immunology* 151(2) :717-729 (Jul. 15, 1993).

Shyjan et al., "Human mucosal addressin cell adhesion molecule-1 (MAdCAM-1) demonstrates structural and functional similarities to the $\alpha_4\beta_7$-integrin binding domains of murine MAdCAM-1, but extreme divergence of mucin-like sequences" *Journal of Immunology* 156(8) :2851-2857 (Apr. 15, 1996).

Springer, T., "Traffic signals for lymphocyte recirculation and leukocyte emigration: the multistep paradigm" *Cell* 76(2) :301-314 (Jan. 28, 1994).

Tanaka et al., "Inhibition of inflammatory liver injury by a monoclonal antibody against lymphocyte function-associated antigen-1" *Journal of Immunology* 151 :5088-5095 (Nov. 1993).

Tidswell et al., "Structure-function analysis of the integrin $\beta_7$ subunit: identification of domains involved in adhesion to MAdCAM-1" *Journal of Immunology* 159(3) :1497-1505 (Aug. 1, 1997).

Viney et al., "Mucosal addressin cell adhesion molecule-1: a structural and functional analysis demarcates the integrin binding motif" *Journal of Immunology* 157(6) :2488-2497 (Sep. 15, 1996).

Walsh et al., "Integrin $\alpha_4\beta_7$ mediates human eosinophil interaction with MAdCAM-1, VCAM-1 and fibronectin" *Immunology* 89(1) :112-119 (Sep. 1996).

*The Leucocyte Antigen FactsBook*, Barclay et al. pp. 298-299 (1997).

Stedman's Medical Dictionary, "www.pdrel.com/pdr/static. htm?path=pdrel/stedmans/c/s07941.htm,s07961. htm,s08043.htm,s31842.htm", Wiliams & Wilkins (1995).

\* cited by examiner

DIAGNOSIS AND TREATMENT OF HEPATIC DISORDERS

This is a continuation in-part application claiming priority to application Ser. No. 09/310,247, filed May 12, 1999 now abandoned which claims the benefit of U.S. Provisional Application No. 60/085,326, filed May 13, 1998, the entire disclosure of which is hereby incorporated by reference.

BACKGROUND OF THE INVENTION

1. Field of the Invention

This invention relates to methods and compositions which can be employed in the prophylaxis, treatment and management of liver disorders, especially those characterized by inflammation. Also disclosed are methods and reagents useful in the prognosis and diagnosis of inflammatory liver disorders.

2. Description of Related Disclosures

The recruitment and recirculation of leukocytes from blood, through tissue, into lymph and back to the blood are key events in the inflammatory process associated with tissue injury, infection or antigen deposition (Springer, T., (1994) Cell, 76:301–314; Berlin et al., (1995) Cell, 80:413–422; Schweighoffer et al., (1993) J. Immunol., 151: 717–729). These events are regulated at a molecular level by interactions between various specialized molecules on the surface of circulating leukocytes and vascular endothelial cells (Springer, T., (1994) supra). Recent models indicate that the recruitment or homing of peripheral blood leukocytes, including lymphocyte subsets, to various tissue sites proceeds by a multistep process comprising i) a primary transient contact event, ii) a rapid activating event that involves G protein-linked signaling receptors and iii) activation triggered firm adhesion (Springer et al., (1994) supra). Chemotaxis and extravasation of leukocytes into tissue follows these three primary events.

The mucosal addressin cell adhesion molecule-1 (MAdCAM-1) is involved in the selective homing of lymphocytes to normal mucosal tissues (Berlin et al., (1993) Cell, 74:185–195; Briskin et al., (1997) Am. J. Pathol. 151: 97–110). It is expressed on a restricted set of vessels including high endothelial venules (HEV's) of the mucosal associated lymphoid tissues and directs lymphocyte traffic to Peyer's patches and the intestinal lamina propria (Berlin et al., (1993) supra). In humans, MAdCAM-1 expression has been associated with tissues of the gastrointestinal tract (colon and small intestine) and associated lymphoid tissues (mesenteric lymph nodes)(Briskin et al., (1997) supra). It has been detected in pancreas, gall bladder and splenic venules and marginal sinus of the splenic white pulp (Kraal et al., (1995) Am. J. Path. 147:763–771). In inflammatory settings increased MAdCAM-1 expression has been observed in HEV like vessels in the pancreas of non-obese diabetic mice (Hanninen A., et al., (1993) J. Clin. Invest 92:2509), on intestinal lamina propria venules from mice with experimentally induced inflammatory bowel disease (Viney J. et al., (1996) J. Immunol. 157:2488–2497; Picarella D., et al., (1997) J. Immunol., 158:2099–2016) and in humans at inflammatory foci associated with ulcerative colitis and Crohn's disease (Briskin et al., (1997) supra). It has not been detected in the majority of normal or inflamed extra-intestinal tissues (Briskin et al., (1997) supra).

The lymphocyte integrin $\alpha 4\beta 7$ has been shown to mediate lymphocyte (memory T cells) adhesion to MAdCAM-1 (Tidwell et al., J. Immunol. 159:1497–1505; Walsh et al., (1996) Immunol. 89:112–119; Berlin et al., (1993) Cell, 74:185–195). The MAdCAM-1/$\alpha 4\beta 7$ interaction has been shown to mediate selectin-independent interaction and rolling of lymphocytes under physiological flow (Berlin et al., (1995) Cell, 80:413–422).

Antibodies to MAdCAM-1 and both the $\alpha 4$ and $\beta 7$ subunit of the $\alpha 4\beta 7$ integrin block lymphocyte binding to cells expressing MAdCAM-1 (Berlin et al., (1993) Cell, 74:185–195). It has been shown that MAdCAM-1/$\alpha 4\beta 7$ blockade reduces lymphocyte trafficking and decreases the severity of the inflammatory infiltrate and the degree of tissue injury in experimental models of chronic inflammatory bowel disease (Picarella et al., (1997) J. Immunol. 158(5):2099–2106; Hesterberg et al., (1996) Gastroenterology 111:1373–1380). Several potent inhibitors of the MAdCAM-1/$\alpha 4\beta 7$ interaction have been proposed for preventing MAdCAM-1 associated leukocyte recruitment to the gastrointestinal tract (International Publication No. WO 96/24673, International Publication No. WO 97/25351).

SUMMARY OF THE INVENTION

The present invention encompasses methods and compositions useful in the diagnosis, prognosis and treatment of hepatic disorders. The methods and compositions of the invention can be employed in the diagnosis, prognosis and treatment of a variety of hepatic disorders, especially those characterized by MAdCAM-1 associated leukocyte recruitment to the liver. Hepatic disorders within the present invention include any systemic disease or disorder characterized by MAdCAM-1 expression including infections, especially viral infections, autoimmune disorders, iatrogenic disorders, hereditary disorders, cholestatic disorders, sarcoidosis, organ transplant and graft versus host disease after bone marrow transplant. The invention is preferably used to treat hepatitis, especially viral hepatitis, and autoimmune hepatitis, cholestatic disorders such as primary biliary cirrhosis and primary sclerosing cholangitis and allograft rejection.

The methods of treatment encompassed within the present invention comprise administration to a host in need thereof of an agent which prevents the interaction of MAdCAM with a MAdCAM binding partner or ligand such as the $\alpha 4\beta 7$ integrin or which inhibits the expression of MAdCAM in the liver. The methods are useful in preventing MAdCAM-1 associated leukocyte recruitment to the liver as well as inhibiting a primary event in the inflammatory response such as blocking interactions between intercellular adhesion molecules and their ligands. In preferred embodiments, the methods of the present invention are employed to reduce or prevent the infiltration of $\alpha 4\beta 7$ bearing leukocytes into liver thereby decreasing the severity of inflammation and the degree of tissue injury in the hepatic disease or disorder treated.

The invention includes compositions, including pharmaceutical compositions comprising agents such as antibodies for the treatment of hepatic disorders as well as kits and articles of manufacture. Kits and articles of manufacture preferably include:

(a) a container;

(b) a label on said container; and (c) a composition comprising an active agent contained within said container; wherein the composition is effective for treating a hepatic disorder, the label on said container indicates that the composition can be used for treating a hepatic disorder, and the active agent in said composition comprises an agent which prevents the interaction of MAdCAM with a ligand therefor. The kits optionally include accessory components such as a second container comprising a pharmaceutically-acceptable buffer and instructions for using the composition to treat a hepatic disorder.

Also disclosed are methods useful in the prognosis and diagnosis of hepatic disorders, especially those characterized by the expression of MAdCAM-1 in hepatic tissue. The diseases or disorders for prognosis or diagnosis under the present invention include those diseases and disorders treatable within the context of the present invention. The diagnostic methods can be employed to detect the presence of MAdCAM-1 in a sample, especially a liver biopsy or the presence of infiltrating leukocytes bearing a ligand for MAdCAM-1 in the sample. The methods can be employed to detect the disorder or to monitor, stage or predict the course of the disease or the therapy used to treat the disorder.

BRIEF DESCRIPTION OF THE DRAWINGS

FIGS. 1A–1C FIG. 1A shows MAdCAM (arrow) expression on high endothelial venules in normal adult human lymph node.

FIGS. 2A–2D Representative disease samples.

DETAILED DESCRIPTION OF THE PREFERRED EMBODIMENTS DEFINITIONS

In general, the following words or phrases have the indicated definition when used in the description, examples, and claims.

"MAdCAM" or "MAdCAM-1" are used interchangeably in the context of the present invention and refer to the protein mucosal addressin cell adhesion molecule-1, which is a single chain polypeptide comprising a short cytoplasmic tail, a transmembrane region and an extracellular sequence composed of three immunoglobulin-like domains. The cDNAs for murine, human and macaque MAdCAM-1 have been cloned (Briskin, et al, (1993) Nature, 363:461–464; Shyjan et al., (1996) J. Immunol. 156:2851–2857).

By "MAdCAM-binding partner or ligand" it is meant a molecule that interacts with MAdCAM. The molecule may be naturally occurring and may be soluble or localized to the surface of a cell. One known MAdCAM ligand is the lymphocyte integrin α4β7 (hereafter, "α4β7"), a heterodimeric structure consisting of an a and a β subunit. The human α4 subunit (Kilger and Holzmann (1995) J. Mol. Biol. 73:347–354) associates with the β7 subunit (Erie et al., (1991) J. Biol. Chem. 266:11009–11016) and is expressed on a majority of mature lymphocytes, as well as a small population of thymocytes, bone marrow cells and mast cells. (Kilshaw and Murant (1991) Eur. J. Immunol. 21:2591–2597 and Gurish et al., (1992) 149: 1964–1972). In the human, the monoclonal antibody ACT-1 (Lazarovits et al., (1984) J. Immunol. 133(4):1857–1862) has been used to identify the α4β7 heterodimer on human T and B cells.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. Further, administration of the agent after onset and after clinical symptoms have developed where administration affects clinical parameters of the disease or disorder, such as the degree of tissue injury or the amount or extent of leukocyte trafficking and perhaps amelioration of the disease, comprises "treatment" of the disease.

Those "in need of treatment" include mammals, such as humans, already having the disease or disorder, including those in which the disease or disorder is to be prevented.

The expressions, "agent", "composition" and "antagonist" are used within the scope of the present invention interchangeably and are meant to include any molecule or substance which prevents the interaction between MAdCAM-1 and a MAdCAM ligand or binding partner such as the leukocyte surface antigen α4β7. Such molecules include small bioorganic molecules, e.g. peptidomimetics, antibodies, immunoadhesins, proteins, peptides, glycoproteins, glycopeptides, glycolipids, polysaccharides, oligosaccharides, nucleic acids, bioorganic molecules, pharmacological agents and their metabolites, transcriptional and translation control sequences, and the like.

The term "inflammation" is used here to refer to reactions of both the specific and non-specific defense systems. A specific defense system reaction is a specific immune system reaction to an antigen. Examples of specific defense system reactions include T cell and antibody response to antigens, such as viruses, and delayed-type hypersensitivity. A non-specific defense system reaction is an inflammatory response mediated by leukocytes generally incapable of immunological memory. Such cells include macrophages, eosinophils and neutrophils. Examples of non-specific reactions include the immediate swelling after a bee sting, and the collection of PMN leukocytes at sites of bacterial infection, e.g., pulmonary infiltrates in bacterial pneumonias and pus formation in abscesses.

The term "iatrogenic disorder" refers to those disorders induced by exposure to a therapeutic compound intended to treat some other disorder. Examples of drug induced liver diseases or disorders include, for example chronic active hepatitis associated with administration of Amineptine, Clometacine, Dantrolene, Diclofenac, Fenofibrate to name but a few; chronic cholestasis associated with the administration of Aceprometazine, Ajmaline and related drugs, Amitryptyline, and Ampicillin to name but a few; or hepatic granulomas associated with administration of Allopurinal, Aspirin, and Diazepam to name but a few. In this context reference can be made to Tables 15.10, 15.8 and 15.11 of Pathology of the Liver, 3rd. Edition, (Macseen, Anthony, Scheuer, Burt and Portman, eds.) Churchill Livingstone (1994) the disclosure of which is incorporated in its entirety herein by reference.

The term "antibody" is used in the broadest sense and specifically covers single monoclonal antibodies (including agonist and antagonist antibodies) and antibody compositions with polyepitopic specificity.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture, uncontaminated by other immunoglobulins.

The monoclonal antibodies herein include hybrid and recombinant antibodies produced by splicing a variable (including hypervariable) domain of one antibody with a constant domain (e.g. "humanized" antibodies) of another antibody, or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. (See, e.g., Cabilly et al., U.S. Pat. No. 4,816,567; Mage and Lamoyi, in *Monoclonal Antibody Production Techniques and Applications*, pp. 79–97 (Marcel Dekker, Inc., New York, 1987).)

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler and Milstein, *Nature* 256:495 (1975), or can be made by recombinant DNA methods (Cabilly et al., supra).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. U.S.A.* 81:6851 (1984)). "Humanized" forms of non-human (e.g., murine) antibodies are specific chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., *Nature* 321:522 (1986); Reichmann et al., *Nature* 332:323 (1988); and Presta, *Curr. Op. Struct. Biol.* 2:593 (1992).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the term "immunoadhesin" designates antibody-like molecules which combine the "binding domain" of a heterologous protein, for example MAdCAM (an "adhesin", for example, a receptor, ligand or enzyme) with the effector functions of immunoglobulin constant domains. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG, IgM, IgE, IgA, and any subclass or isotype thereof.

MODES FOR CARRYING OUT THE INVENTION

Hepatic Diseases and Disorders

The methods of the invention are useful in the diagnosis, prognosis and treatment of a variety of hepatic disorders, in particular those characterized by the presence of MAdCAM bearing cells. Therefore, according to the present invention, a hepatic disorder is any liver disease or disorder accompanied by the expression of MAdCAM-1 in the liver and surrounding vasculature. For example, the methods of the invention are useful in the diagnosis, prognosis and treatment of variety of hepatic disorders including those resulting from infection, iatrogenic disorders, hereditary disorders, autoimmmune disorders, cholestatic syndromes, sarcoidosis, organ transplantation, and the like so long as the disorder is characterized by the presence of MAdCAM-1 bearing cell types.

Diseases or disorders within the scope of the present invention include but are not limited to the diseases and disorders detailed in Table I.

TABLE I

Systemic Diseases and Disorders Involving Liver Inflammation

A. Hepatitis

1. Any inflammation of the liver, as for example in acute hepatitis, chronic hepatitis, alcoholic hepatitis and cirrhosis.
2. Infection
   -Any inflammation of the liver resulting from infection, especially viral infection, especially chronic viral hepatitis, for example inflammation associated with:
   a) Hepatitis A, picorna virus
   b) Hepatitis B, hepadna virus (hepatocellular carcinoma)
   c) Hepatitis C, flavivirus
   d) Hepatitis D (Δ), incomplete RNA virus (requires co-infection with hepatitis B)
   e) Hepatitis E, single stranded, positive sense RNA genome
   f) Hepatitis F,
   g) Hepatitis G (HGBV-C) single stranded RNA virus
   h) Epstein-Barr virus
   i) cytelomegalovirus
   j) adenovirus
   k) other viral infections of the liver
3. Autoimmune
   -Any inflammation of the liver associated with autoimmune onset of known or unknown etiology, typically associated with significant lymphocyte infiltration in the portal tracts and associated piecemeal necrosis.
4. Iatrogenic
   -Any drug induced liver inflammation, including for example, chronic active hepatitis, cholestasis or granuloma formation.
5. Hereditary
   -Any inflammation associated with gene-linked trait, for example cirrhotic changes in the liver associated with hepatolenticular degeneration,
   a) Wilson's disease
   b) α 1-antitrypsin deficiency
   c) other inherited metabolic disorders, for example, galactosemia B. Cholestatic Syndromes -Any inflammation of the intrahepatic bile ducts, including those resulting in hepatic dysfunction and cirrhosis as for example in primary biliary cirrhosis, primary sclerosing cholangitis and adult idiopathic ductopenia C. Transplantation -Any inflammation of the liver or hepatic ducts including that associated with hepatic transplantation, liver injury in graft versus host disease and recipients of renal and other allografts, for example hyperacute allograft rejection, and xenograft rejection.

Particularly preferred disorders within the context of the invention are chronic hepatitis particularly hepatitis resulting from infection, particularly viral infection. Included in this category are the established serological categories of chronic hepatitis, including viral (HBV, HDV, HCV), autoimmune hepatitis (classic lupoid type and subtypes), autoimmune overlap syndromes, drug induced (for example nitrofurantoin, alpha methyldopa, isoniazid) and so-called "cryptogenic" hepatitis. In this regard the skilled artisan will make reference to chapter 9, and especially Tables 9.2 and 9.3 in Pathology of the Liver, 3rd. Edition, (Macseen, Anthony, Scheuer, Burt and Portman, eds.) Churchill Livingstone (1994) the disclosure of which is incorporated in its entirety herein by reference. As the skilled artisan will recognize, some chronic liver diseases not included within the definition of chronic hepatitis may have histological features of chronic hepatitis (for example, piecemeal necrosis). These disorders such as, for example, diseases of intra or extrahepatic bile ducts, are included within the definition herein. Infection with a number of viruses is known to result in serious inflammation of the liver including the hepatitis viruses, hepatitis A (HAV), hepatitis B (HBV), hepatitis C (HCV), hepatitis D (HDV, delta agent) hepatitis E, hepatitis F and other viruses such as Epstein-Barr virus, cytomegalovirus, adenovirus, paramyovirus, and the like. At least seven types of hepatitis virus (designated A–G) have been identified to date. Of these, one of the most devastating is hepatitis C virus (HCV, also called non-A, non-B). An estimated 3.9 million people in the US are currently infected with HCV, and an estimated 8,000–10,000 deaths each year result from HCV-associated chronic liver disease. Current therapies include γ-interferon, emphasize B and ribivirin, each of which have limited efficacy and serious side effects. Current therapy also includes transplantation, however, since the infected individual remains infected with the virus, post-transplant immunosuppressed patients exhibit increased viral RNA levels and often rapidly progress to liver disease with the new liver.

Chronic cholestatic syndromes are characterized by progressive inflammatory destruction of intrahepatic bile ducts resulting in hepatic dysfunction, fibrosis and cirrhosis. Examples of this type of disorder include primary biliary cirrhosis, primary sclerosing cholangitis and adult idiopathic ductopenia.

Hereditary disorders treatable by the methods disclosed herein include those inflammatory disorders associated with a gene-linked trait. Examples include Wilson's disease, α1-antitrypsin deficiency and inherited metabolic disorders such as galactosemia and tyrosineanemia.

Diagnosing and Prognosing a Hepatic Disorder

Hepatic disorders for prognosis and diagnosis within the context of the present invention are described above and are characterized by the presence of MAdCAM in a sample, for example a sample of hepatic tissue or surprisingly in a cell free sample such as serum. Therefore, one embodiment of the present invention is directed to the detection and/or measurement of MAdCAM in a sample and the use of such detection or measurement in the diagnosis, staging, determination of severity, and prognosis in general of the hepatic disease or disorder. Further, since the expression of MAdCAM has been shown to correlate with the presence of lymphocytes bearing the α4β7 integrin, prognosis and diagnosis of hepatic disorders within the context of the present invention encompass the measurement or detection of the presence of lymphocytes bearing α4β7 integrin.

A. Detecting Soluble or Cell-free MAdCAM

The present invention includes a method for diagnosis and prognosis of diseases and disorders not limited to hepatic diseases and disorders but appropriately used therefor, based upon the discovery that MAdCAM can be detected in the serum of a subject. Therefore the present invention includes methods of diagnosis and prognosis of diseases or disorders characterized by the expression of MAdCAM bearing cell types in general and which include but are not limited to the hepatic diseases or disorders listed above.

According to this aspect of the present invention, a sample which is subjected to testing is a sample derived from a subject such as a human and includes, but is not limited to, any biological fluid, preferably a bodily fluid. Especially preferred are cell-free samples, the term cell-free being used herein to indicate that the sample is substantially devoid of cells or that the sample is substantially free of cell types bearing MAdCAM. Examples of bodily fluids include, but are not limited to, whole blood, serum, plasma, urine, synovial fluid, cranial or spinal fluid, saliva, tissue infiltrate, cervical or vaginal exudate, tissue infiltrate, pleural effusions, bronchoalveolar lavage fluid, gastric lavage fluid, small or large bowel contents, fecal preparations, and the like. In another embodiment, the biological fluid may be a cell culture medium or supernatant of cultured cells. Preferably the sample is a blood sample and especially a serum sample. The methods provided by the present invention overcome many of the limitations of prior art methods of measuring or detecting MAdCAM, which heretofore required samples comprising cells followed by immunohistochemical techniques or direct or indirect immunofluorescence analysis by microscopy or flow cytometry. Limitations of the prior art procedures include the requirement for: (1) fairly rare tissue samples comprising a large number of cells, (2) extensive preparation time, and (3) expensive equipment, such as a flow cytometer. The methods provided herein overcome these limitations.

Any procedure known in the art for the measurement of analytes can be used in the practice of the measurement of MAdCAM in a sample. Such procedures include but are not limited to competitive and non-competitive assay systems using techniques such as radioimmunoassays, enzyme immunoassays (EIA), preferably the enzyme linked immunosorbent assay (ELISA), "sandwich" immunoassays, precipitin reactions, gel diffusion reactions, immunodiffusion assays, agglutination assays, complement-fixation assays, immunoradiometric assays, fluorescent immunoassays, protein A immunoassays, and immunoelectrophoresis assays, to name but a few. For examples of preferred immunoassay methods, see U.S. Pat. No. 4,845,026 (Jul. 4, 1989) and U.S. Pat. No. 5,006,459 (Apr. 9, 1991).

For diagnostic and prognostic applications, a MAdCAM binding partner, typically an antibody will be labeled with a detectable moiety and used to detect MAdCAM in a sample as described above. Numerous labels are available which can be preferably grouped into the following categories:

(a) Radioisotopes, such as $^{35}S$, $^{14}C$, $^{125}I$, $^{3}H$, and $^{131}I$. The MAdCAM binding partner such as an antibody can be labeled with the radioisotope using the techniques described in *Current Protocols in Immunology*, Volumes 1 and 2, Coligen et al., Ed., Wiley-Interscience, New York, N.Y., Pubs., (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the MAdCAM binding partner such as an antibody using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme preferably catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73: 147–166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

In the assays of the present invention, a MAdCAM binding partner such as an antibody is preferably bound to a solid phase support or carrier. By "solid phase support or carrier" is intended any support capable of binding an antigen or antibodies. Well-known supports, or carriers, include glass, polystyrene, polypropylene, polyethylene, dextran, nylon, amyloses, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

In a preferred embodiment, an antibody-MAdCAM-antibody sandwich immunoassay is done, i.e., MAdCAM is detected or measured by a method comprising binding of a first antibody to the MAdCAM antigen, and binding of a second antibody to the MAdCAM, and detecting or measuring MAdCAM immunospecifically bound by both the first and second antibody. In a specific embodiment, the first and second antibodies are monoclonal antibodies. In this embodiment, the second monoclonal antibody preferably binds to a site different from that of the first antibody (as reflected e.g., by the lack of competitive inhibition between the two antibodies for binding to the antigen). In another specific embodiment, the first or second antibody is a polyclonal antibody. In yet another specific embodiment, both the first and second antibodies are polyclonal antibodies.

In a preferred embodiment, a "forward" sandwich enzyme immunoassay is used, as described schematically below. An antibody (capture antibody, Ab1) directed against the MAdCAM is attached to a solid phase matrix, preferably a microplate. The sample is brought in contact with the Ab1-coated matrix and such that any MAdCAM in the sample to which Ab1 is specific binds to the solid-phase Ab1. Unbound sample components are removed by washing. An enzyme-conjugated second antibody (detection antibody, Ab2) directed against a second epitope of the MAdCAM binds to the antigen captured by Ab1 and completes the sandwich. After removal of unbound Ab2 by washing, a chromogenic substrate for the enzyme is added, and a colored product is formed in proportion to the amount of enzyme present in the sandwich, which reflects the amount of MAdCAM in the sample. The reaction is terminated by addition of stop solution. The color is measured as absorbance at an appropriate wavelength using a spectrophotometer. A standard curve is prepared from known concentrations of the MAdCAM, from which unknown sample values can be determined.

Other types of "sandwich" assays are the so-called "simultaneous" and "reverse" assays. A simultaneous assay involves a single incubation step as the antibody bound to the solid support and labeled antibody are both added to the sample being tested at the same time. After the incubation is completed, the solid support is washed to remove the residue of fluid sample and uncompleted labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

B. Diagnostic and Prognostic Methods in General

The methods of the present invention can be used alone or in conjunction with other diagnostic tests for the diagnosis and detection of a hepatic disorder. Viral infections can be detected using techniques known in the art. Hepatitis C infection, for example, can be detected using commercially available serologic assays which detect anti-HCV antibodies or molecular assays which detect HCV RNA genomes within an infected patient. The methods of present invention can be used alone or in conjunction with these routine tests as an aid in diagnosis. As another example, in many cases the specific cause of a liver disorder is identified on the basis of elevated liver function tests or an enlarged liver. The diagnostic methods of the present invention can be used alone or in conjunction with these tests to diagnose a disease or disorder within the context of the present invention. As but a further example, blood tests and a liver biopsy are routinely used to diagnose or confirm a diagnosis and as well to determine the amount, extent and severity of damage to the liver. The diagnostic methods of the present invention can be used alone or in conjunction with these tests in determining the amount, extent, or severity of damage to the liver.

Somewhat more particularly, a diagnostic tests performed on for example a serum sample, an in vivo sample or a liver biopsy can, with the present invention, be extended to the detection of MAdCAM expression in the sample. Further, the detection of MAdCAM in the sample can be used to monitor the course or progression of the disease as well as the course of or effectiveness of a therapeutic treatment.

In a particular embodiment, the diagnostic techniques described can be used to follow the progress of therapy. In a subject undergoing therapeutic treatment that results in an increase or a decrease in the amount of trafficking lymphocytes, the amount of lymphocyte trafficking may serve as a useful measure for the success or failure of the treatment. Thus, the present invention provides a method for monitoring the effect of a therapeutic treatment in a subject which comprises measuring at suitable time intervals the amount of MAdCAM expressed in a sample of liver tissue or conversely the amount or number of lymphocytes in the sample. The total amount of MAdCAM or $\alpha 4\beta 7$ is compared to a "baseline" or "control" value which depending on the disease, and the treatment, may be the amount of MAdCAM in a similar sample from a normal subject, from the patient prior to disease onset or during remission of disease, or from the patient prior to the initiation of therapy. One of ordinary skill in the art will readily discern the appropriate baseline value to use in a particular situation without undue experimentation.

A preferred subject for the methods of the present invention is a vertebrate, including but not limited to a mammal, fish, amphibian, reptile, bird, marsupial, and most preferably, a human either fetal or adult human liver. Thus the methods and kits of this invention are applicable to human clinical and veterinary uses.

According to a particular aspect of the present invention, a sample, for example a liver biopsy sample is derived from a subject by methods routine to those skilled in the art. The most common way a liver sample is obtained is by liver biopsy, a procedure used to obtain a small amount of liver tissue which can be subsequently examined employing routine immunohistochemical techniques in conjunction with the methods of the present invention. For example liver sample can be obtained by needle biopsy directly into the liver of subject, or for example by guiding a needle into the liver of the subject through the abdomen or chest using various imaging techniques known to the skilled artisan. Less commonly, samples are obtained using techniques such as laproscopy, transvenous or transjugular liver biopsy and surgical liver biopsy.

As noted above any procedure known in the art for the measurement of analytes can be used in the practice of the instant invention to detect the presence of MAdCAM or a ligand therefor, such as $\alpha 4\beta 7$. Such procedures include but are not limited to immunohistochemical techniques known to those skilled in the art, competitive and noncompetitive assay systems using techniques such as radioimmunoassays, enzyme immunoassays (EIA), preferably the enzyme linked immunosorbent assay (ELISA), "sandwich" immunoassays, precipitin reactions, gel diffusion reactions, immunodiffusion assays, agglutination assays, complement fixation assays, immunoradiometric assays, fluorescent immunoassays, protein A immunoassays, and immunoelectrophoresis assays, to name but a few.

Kits comprising one or more containers or vials containing components for carrying out the assays of the present invention are also within the scope of the invention. For instance, such a kit can comprise reagents required for the immunohistochemical analysis of a sample such as a liver biopsy. Reagents may include one or more binding partners, e.g., an antibody or antibodies, to antigen, for example a leukocyte integrin or other MAdCAM binding partner, or MAdCAM itself. For histological assays the kit contains the chromogenic substrate as well as a reagent for stopping the enzymatic reaction when color development has occurred. The substrate included in the kit is one appropriate for the enzyme conjugated to one of the antibody preparations such as an anti-human MAdCAM antibody. These are well-known in the art. The kit can optionally also comprise a standard; i.e., a known amount of purified MAdCAM.

In another embodiment, a kit can comprise more than one set of reagents. For example a kit can comprise a pair of antibodies or other binding partners, each pair directed against a different target molecule, thus allowing the detection or measurement of a plurality of such target molecules in a sample, for example, MAdCAM and a liver cell-specific surface protein or MAdCAM and α4β7.

Compositions

Compositions useful in the therapeutic and the diagnostic methods of the present invention, are available to the skilled artisan and can be identified based upon their ability to prevent, block or suppress MAdCAM mediated cell adhesion. The compositions are useful in the treatment and diagnosis of hepatic disorders associated with that adhesion, such as inflammation and immune reactions.

It will be understood that appropriate agents able to prevent, block or suppress MAdCAM mediated cell adhesion may accomplish this effect in various ways. Without limitation to a particular theory, one class of agents will bind to MAdCAM-1 with sufficient affinity and specificity to prevent interaction with lymphocytes expressing a naturally occurring ligand for MAdCAM such as the lymphocyte integrin α4β7. Another class of agents will bind to a naturally occurring leukocyte ligand for MAdCAM such as the lymphocyte integrin α4β7 and thereby prevent its interaction with MAdCAM.

Exemplary agents are antibodies preferably a monoclonal, chimeric and or humanized antibody or an antigen binding fragment thereof which inhibits adhesion of leukocytes to MAdCAM. A further exemplary agent is a soluble MAdCAM molecule or a molecule based upon MAdCAM such as a soluble form of MAdCAM comprising the integrin binding site of MAdCAM or a MAdCAM immunoadhesin comprising, for example, the extracellular domain of MAdCAM fused to an immunoglobulin constant domain.

As a further example of an agent, a peptide or a molecule based upon a peptide sequence present in MAdCAM and required for integrin binding can be used as an agent within the context of the present invention. The amino acid motif GLDTSL conserved and present in Ig-like adhesion receptors including human MAdCAM can be used to design appropriate agents. International Publication Number WO 97/25351 provides molecules of this type which mimic the conserved amino acid motif LDTSL of MAdCAM. Alternatively, it has been shown that integrins can selectively bind a variety of Arg-Gly-Asp (RGD) containing ligands. RGD-based peptide inhibitors with different structures can be prepared which are effective agents within the context of the present invention (Jackson et al., (1997) J. Med. Chem. 40:3359–3368).

A further agent is an antisense nucleic acid, which is complementary, in whole or in part, to a target molecule comprising a sense strand, and can hybridize to the target molecule. When introduced into a cell antisense nucleic acid can inhibit the expression of the gene encoded by the sense strand. Antisense nucleic acid in whole or in part complimentary to the nucleic acid sequence of MAdCAM such as those described in International Publication No. WO 96/24673 can be produced for this purpose.

In a preferred embodiment the agent is an antibody, which antibody has the desirable properties of binding to MAdCAM-1 and preventing its interaction with the leukocyte associated ligand. Useful antibodies are available to the skilled artisan such as those described herein or those described by Podolsky et al., (1993) J. Clin. Invest. 92(1): 372–380; Picarella et al., (1997) J. Immunol. 158:2099–2106; and Hesterberg et al., (1996) Gastroenterology 111:1373–1380. The following techniques can, without limitation, be employed in identifying and isolating appropriate agents useful in blocking or preventing the interaction between MAdCAM-1 and a MAdCAM binding partner. The compositions of the invention can be assayed by techniques known in the art in order to demonstrate their activity. Such assays include, but are not limited to, the following in vitro tests for the ability to interact with MAdCAM proteins, to inhibit MAdCAM related activity, or to selectively inhibit the generation of MAdCAM derived peptides. In vitro methods include a protein based assay such as that described in Berlin et al., (1993) Cell 74:185–195 where purified MAdCAM is applied to glass slides for binding assays. Agents within the context of the present invention inhibit the binding of normal lymphocytes to the immobilized MAdCAM.

In another appropriate assay purified α4β7 is immobilized on a solid support such as a glass slide or a plastic plate pre-incubated with an antibody to α4 subunit that does not block interaction of the integrin with MAdCAM. In this assay MAdCAM or preferably a MAdCAM-immunoglobulin chimera is incubated with the immobilized integrin in the presence or absence of a suspected agent. The binding or absence of binding of MAdCAM in the presence of the agent being tested can then be measured with a detecting agent such as an anti-MAdCAM or anti-Ig antibody.

Alternatively a cell based assay employing a cell transfected with the α4β7 integrin subunits and which expresses the intact integrin can be used in a cell based assay for identification of appropriate agents. For instance, the ability of a monoclonal antibody to inhibit adhesion of the natural cellular ligands to the cells expressing MAdCAM or the α4β7 integrin can be used. Typically, the agent of the invention is incubated with the MAdCAM/α4β7-bearing cells in the presence of the natural receptor/ligand-bearing cells, wherein the MAdCAM-bearing cells have been immobilized on a solid support. Inhibition of the cellular adhesion is then assessed by either calculating the amount of the bound mAb or assessing the displaced cells.

Agents effective in blocking or preventing the association of MAdCAM with lymphocytes may be identified by in vivo assays such as a model utilizing cotton-top tamarins. Cotton-top tamarins (CTT's; *Saguinus oedipus*) are a New World nonhuman primate species that, in captivity, develop spontaneous and often chronic colitis that clinically and histologically resembles ulcerative colitis in humans (Madera et al., (1985) Gastroenterology 88:13–19). This model has been used to show that the murine anti-human monoclonal antibody ACT-1 (Lazarovits et al., (1984) *J. Immunol.* 1331857) to α4β7 cross reacts with CTT α4β7 and reduces leukocyte cell density in inflamed colonic mucosa, attenuates histological inflammatory activity, and rapidly resolves clinical disease. Thus it will be useful in identifying additional substances that interfere with the interaction between hepatic-expressed MAdCAM and a MAdCAM ligand.

A lymphocyte homing assay such as that associated with the murine tri-nitro-benzene sulfonic acid (TNBS) induced colitis model and described in Viney et al., (1996) *J. Immunol.* 157:2488–2497 may be appropriate for the identification of agents and compositions.

The specificity or discrimination between two or more competing substrates is determined by the ratios of bound to unbound. For example, according to a cellular assay such as those described herein, radiolabeled or flourescent labeled α4β7 is incubated with immobilized MAdCAM-1 receptor-immunoglobulin chimeras in varying concentration of unlabeled candidate compound. Increasing concentrations of successful candidate molecule effectively prevent binding of labeled α4β7 to immobilized receptor chimeras. The concentration of unlabeled agent at which 50% maximal α4β7 is displaced is referred to as the EC50 and reflects the receptor binding affinity. Therefore a candidate compound with an EC50 of 100 nM displays a substantially weaker interaction with a receptor than candidate agent with an EC50 of 10 nM. This discrimination in substrate specificity indicates that the preferred agent or antagonist has utility in, for example, preventing or blocking the interaction of MAdCAM with leukocyte surface antigens and especially α4β7 in a setting where both the natural ligand and the so-called agent or antagonist are present.

An exemplary agent is a monoclonal antibody reactive with α4β7 or MAdCAM. Antibodies are assessed by affinity constants. Affinity constants are a measure of the interaction between a particular ligand and its cognate receptor. The "binding affinity" or the measure of the strength of association between a particular receptor ligand interaction is generally measured by affinity constants for the equilibrium concentrations of associated and dissociated configurations of the ligand and its receptor The present invention contemplates such an interaction between an agent or composition and the endothelial cell adhesion molecule MAdCAM-1. In general, the dissociation constants of ligand/integrin interactions in solution are relatively weak and range from low micromolar to high nanomolar. Additivity of multiple adhesive interactions at a cell surface, or the "avidity," provides the necessary binding energy to anchor leukocytes to the vascular endothelium. Therefore, in general, a useful composition or agent has a higher affinity for the integrin receptor than its native ligand. Such an antagonist blocks or prevents a high percentage of the cell surface interactions involved in cellular adhesion mediated by the α4β7/MAdCAM-1 interaction. Preferably the binding of the agent or antagonist should occur at an affinity of about $k_a=10^{-4}$M or greater to be useful for the present invention, with greater than about $10^{-8}$M being more preferable, and most preferably between about $10^{-8}$M and about $10^{-10}$M.

As additional criteria, those forms of the molecule that are readily absorbed by tissues, that are protected from rapid metabolism and/or that provide for prolonged half life, are preferentially selected in producing the compositions of the invention. One skilled in the art may also effect modifications of the protein formulation, to effect absorption. These modifications include, but are not limited to, use of a pro-drug and chemical modification of the primary structure (Wearley, L. L., 1991, Crit. Rev. in Ther. Drug Carrier Systems, 8(4):333). In minimizing metabolism of the protein and thereby increasing the effective amount of protein, such modifications include but are not limited to chemical modifications and covalent attachment to a polymer (Wearley, L. L., 1991, supra).

Therapeutic Methods and Pharmaceutical Compositions

While not intending to be limited by a mechanism of action, it is believed that migration of activated leukocytes from the blood stream into the liver tissue is dependent on the interaction of the lymphocytes with the MAdCAM in the liver tissue. Leukocyte traffic across the vessel walls to extravascular vascular tissue is necessary for host defense against microbial organisms or foreign antigens and repair of tissue damage. Under some circumstances, however, leukocyte-endothelial interactions may have deleterious consequences for the host. During the process of adherence and transendothelial migration, leukocytes may release products such as oxidants, proteases, or cytokines that directly damage endothelium or cause endothelial damage by releasing a variety of inflammatory mediators. The interaction of MAdCAM-1 with leukocyte surface molecules, such as α4β7, facilitates leukocyte migration and contributes to the destructive effects of the inflammatory process.

Therefore, according to the present invention, agents that prevent the interaction between hepatically expressed MAdCAM and ligands such as α4β7 can be employed to treat these types of disorders in the liver.

Additionally, the pharmaceutical compositions of the present invention can be used to eliminate or block the injury occurring in transplanted livers.

The preclinical and clinical therapeutic use of the present invention in the treatment of diseases or disorders associated with MAdCAM will be best accomplished by those of skill, employing accepted principles of diagnosis and treatment. Such principles are known in the art, and are set forth, for example, in Braunwald et al., eds., Harrison's Principles or International Medicine, 11th Ed., McGraw-Hill, H. Y. (1987).

The most effective mode of administration and dosage regimen of agent will depend on the type of disease to be treated, the severity and course of the disease, whether the agents are administered for prophylactic or therapeutic purposes, previous therapy, the patient's clinical history and response to the agents such as antibodies, and the discretion of the attending physician. The agent is suitably administered to the patient at one time or over a series of treatments.

For most therapeutic applications, the agents may be administered to a mammal, preferably a patient, in a pharmaceutically acceptable dosage form, including those that may be administered to a patient intravenously as a bolus or by continuous infusion over a period of minutes, hours, days, weeks, or months, intramuscularly, subcutaneously, intra-articularly, intrasynovially, intrathecally, or periostally, or by oral, topical, or inhalation routes.

A dose of agent may be administered to the patient in one or more single administrations, continuous infusion, or bolus injection. For example, an initial dose of the agent is administered to the patient by injection or infusion. For repeated administrations over several days or longer, depending on the condition, the treatment is repeated until a desired suppression of disease symptoms occurs. However, other dosage regimens may be useful. According to another embodiment of the invention, the effectiveness of the agent may be improved by administering the agent serially or in combination with another agent that is effective for this purpose (for example, interferon γ).

The compositions of the present invention may be part of a delivery system such as liposomes. Delivery systems involving liposomes are discussed in International Patent Publication No. WO 91/02805 and International Patent Publication No. WO 91/19501, as well as U.S. Pat. No. 4,880,635 to Janoff et al. These publications and patents provide useful descriptions of techniques for liposome drug delivery.

The compositions of the invention can be administered to a subject in need thereof to treat the subject by either prophylactically preventing a disease state or relieving it after it has begun. The pharmaceutical compositions of the invention may be administered in any suitable manner, including parental, topical, oral, or local (such as aerosol or transdermal) or any combination thereof. The compositions are preferably administered with a pharmaceutically acceptable carrier, the nature of the carrier differing with the mode of administration, for example, oral administration, usually using a solid carrier and I.V. administration a liquid salt solution carrier.

The compositions of the present invention include pharmaceutically acceptable components that are compatible with the patient and the protein and carbohydrate moieties of the compositions of the invention. These generally include suspensions, solutions and elixirs, and most especially biological buffers, such as phosphate buffered saline, saline, Dulbecco's Media, and the like. Aerosols may also be used, or carriers such as starches, sugars, microcrystalline cellulose, diluents, granulating agents, lubricants, binders, disintegrating agents, and the like (in the case of oral solid preparations, such as powders, capsules, and tablets).

As used herein, the term "pharmaceutically acceptable" preferably means approved by a regulatory agency of the Federal or a state government or listed in the U.S. Pharmacopeia or other generally recognized pharmacopeia for use in animals, and more particularly in humans.

The formulation of choice can be accomplished using a variety of the aforementioned buffers, or even excipients including, for example, pharmaceutical grades of mannitol, lactose, starch, magnesium stearate, sodium saccharin cellulose, magnesium carbonate, and the like. "Peglation" of the compositions may be achieved using techniques known to the art (see for example International Patent Publication No. WO92/16555, U.S. Pat. No. 5,122,614 to Enzon, and International Patent Publication No. WO92/00748). Oral compositions may be taken in the form of solutions, suspensions, tablets, pills, capsules, sustained release formulations, or powders.

A sufficient amount of the compositions of the invention should be administered to the patient to ensure that a substantial amount of the interaction between MAdCAM and a binding partner is inhibited. In this way, hepatic inflammation can either be prevented or ameliorated. The selection of compositions, frequency of administration, and amount of composition so administered will be in accordance with the particular disease being treated and its severity, the type of agent employed, the method of administration, the overall condition of the patient, and the judgment of the treating physician. Typical dosing regions will be analogous to treatment of these disease states by the use of antibodies and other biologicals. Typically, the compositions of the instant invention will contain from about 1% to about 95% of the active ingredient, preferably about 10% to about 50%. Preferably, the dosing will be between about 1–100 mg/kg. About 1 mg to about 50 mg will be administered to a child, and between about 25 mg and about 1000 mg will be administered to an adult. Other effective dosages can be readily determined by one of the ordinary skill in the art through routine trials establishing dose response curves.

In determining the dosage of compositions to be administered, it must be kept in mind that one may not wish to completely block all of the MAdCAM molecules, or may wish to completely block such receptors for only a limited amount of time. In order for a normal healing process to proceed, at least some of the white blood cells or neutrophils must be brought into the tissue in the areas where the wound, infection or disease state is occurring. Thus, the dose of the composition administered as a blocking agent must be adjusted carefully based on the particular needs of the patient while taking into consideration a variety of factors such as the type of disease that is being treated.

Thus, an effective amount of a composition in accordance with the present invention is an amount effective to inhibit the interaction between MAdCAM and a MAdCAM-binding partner.

The following examples are offered by way of illustration and not by way of limitation. The disclosures of all citations in the specification are expressly incorporated herein by reference.

EXAMPLES

Example 1

Generation of Anti-MAdCAM Antibodies

The following example describes the generation of MAdCAM-specific antibodies.

A portion of the MAdCAM protein was expressed as a fusion with a Hisx6 tag on the amino terminus. This chimera was expressed in *E. coli* and the purified protein used to immunize rabbits. These antibodies are useful as diagnostic and/or therapeutic agents.

Methods—

PCR primers were designed to isolate nucleotides 1–675 of full-length human MAdCAM (Shyjan, et al, (1996) J of Immunol. 156:2851–2857. Cloning linkers (EcoR1 and BamH1) and a stop codon were added to the cDNA via PCR. The resulting PCR product (called Human MAdCAM-2D-stop) was subcloned into the EcoR1-BamH1 sites of a pProEX expression vector (Gibco-BRL) for expression in *E. coli* strain DH5α (ATCC 53868). Human MAdCAM-2D-stop was expressed in DH5α cells following IPTG induction according to the protocol from the manufacturer (Gibco-BRL). The cells were then processed and the Hisx6 tagged protein (BAC2D) purified using a Ni-NTA resin, both according to the manufacturer (Gibco-BRL). An SDS PAGE analysis was performed on the purified fraction and a band of approximately 25,000 daltons was observed (predicted wt. 26,689 daltons). The amino acid analysis of the amino terminus gave the expected sequence, confirming the identity of the protein.

To generate antibodies, two New Zealand White rabbits were immunized with 100 g BAC2D in Freund's Complete Adjuvant. The rabbits were boosted with 100 µg of BAC2D in Freund's Incomplete Adjuvent three weeks and six weeks later. Sera were collected and the anti-MAdCAM antibodies isolated by affinity chromatography on protein A sepharose.

The specificity of the antibodies was test by comparing binding to fusion proteins of several adhesion molecules: MAdCAM-1-IgG, VCAM-1-IgG and ICAM-1-IgG. Microtiter plates (96 well, NUNC MaxiSorp) were coated with 100 µl of 2 µg/ml of either MAdCAM-1-IgG, VCAM-1-IgG and ICAM-1-IgG for 2 hours at room temperature. The wells were blocked with 200 µl of 5 mg/ml of bovine serum albumin (BSA) in phosphate buffered saline (PBS) (BSA buffer) for 1 hour at room temperature. Purified rabbit anti-BAC2D antibody or control rabbit IgG (100 µl) were added and diluted serially two fold in BAS buffer. The plates were incubated for 1 hour at room temperature after which the wells were washed three times with 200 µl of 011% Tween in PBS (wash buffer). A solution containing 1:2000 goat anti-rabbit-alkaline phosphatase antibody in PBS (Caltag Cat No. L42008, 100 µl) was added to each well for 1 hour at room temperature. The wells were then washed three times with 200 µl wash buffer and 100 µl substrate (p-nitrophenyl phosphate disodium) added. OD readings were taken at 405 nm.

Results—

Anti-BAC2D bound to MAdCAM coated wells in a concentration dependent manner. However, no binding was observed for either VCAM-1 or ICAM-1 at any concentration, indicating that the anti-BAC2D antibody is specific for MAdCAM.

Generation of Monoclonal Anti-human MAdCAM Antibodies

A group of Balb/c female mice (Charles River Breeding Laboratories, Wilmington, Mass.) were injected with 10 μg/dose of purified MAdCAM and domains 1 and 2 in 100 μl Detox adjuvant (RIBI ImmunoChem Res. Inc., Hamilton, MT) by intraperitoneal injection on days 0, 7, 14, 28, 35, 42, 56, 63, 70, 77, 84, and 91. A pre-fusion boost was given on day 105 to a first animal, on day 126 to a second animal and on day 166 to a third animal. The animals were sacrificed 3 days after the pre-fusion boost. The spleen was removed, and the lymphocytes fused with the mouse myeloma line 653, Kearney et al., *J. Immunol.*, 123:1548 (1979) using 50% polyethylene glycol 1450 (Sigma) by an established procedure (Oi and Herzenberg, in *Selected Methods in Cellular Immunology*, B. Mishel and S. Schiigi, eds., p. 351, W.J. Freeman Co., San Francisco, Calif., (1980). The fused cells were plated into 96-well microtiter plates at a density of $2\times10^5$ cells/well followed by HAT selection, Littlefield, J. W., *Science*, 145:709 (1964)) on day 1 post fusion.

Another group of female mice (Charles River Breeding Laboratories, Wilmington, Mass.) were injected with 5 μg purified MAdCAM and domains 1 and 2 in 100 μl Detox adjuvant (R101) in rear foot pads on days 0, 7, 14, 28, 35, 42, 56, 63, 70, 77, 84 91 and 159. On day 162, all animals were sacrificed, popliteal nodes removed and lymphocytes fused as noted above.

Immobilized hybridoma culture supernatants were reacted with MAdCAM. The wells positive for anti-human MAdCAM antibodies were expanded for further study. These cultures remained stable when expanded. Cell lines were cloned by limiting dilution and cryopreserved. The parental cultures were isotyped and assayed for their ability to capture MAdCAM.

Results

The following anti-human MAdCAM antibodies were obtained.

| Clone # | Isotype | Epitope | Block Function | Usefulness in Immunohistology Frozen | Usefulness in Immunohistology Fixed |
|---|---|---|---|---|---|
| Mmc1 | IgG1 | A1 | No | Yes | Yes |
| Mmc2 | IgG1 | A2 | No | Yes | NT |
| Mmc3 | IgG1 | B | Yes | Yes | Yes |
| Mmc4 | IgG1 | C1 | No | Yes | Yes |
| Mmc6 | IgG$_{2b}$ | D | No | Yes | No |
| Mmc7 | IgG1 | C1 | No | Yes | Yes |
| Mmc8 | IgG1 | C2 | No | NT | NT |

NT = not tested

The specificity of the antibodies produced by the hybridomas were tested by direct incubation with MAdCAM in a standard ELISA. In this assay wells of a flat bottomed 96 well plate were coated overnight at 4° C. with 100 μl of a solution containing purified human MAdCAM at approximately 1 μg/ml in carbonate buffer, pH 9.6. The plate has blocked for 1 h with a solution of 1% BSA in PBS, then washed with wash buffer (0.05% Tween-20 in PBS). Monoclonal antibody purified from ascites generated from hybridomas as well as isotype matched controls were added to the wells and the plate was incubated for 1–2 hours at room temperature. The wells were washed and a solution containing approximately 1 μg/ml horseradish peroxidase (HRP)-conjugated goat anti-mouse specific antibodies (Boehringer Mannheim, Indianapolis, Ind.), 0.5% BSA and 0.25% NP-40, in wash buffer was added and the plates incubated for 2 h. After washing, the plates were developed by addition of a solution containing 0.4 μg.ml o-phenylenediamine dihydrochloride plus 0.4/μl/ml 30% hydrogen peroxide. The reaction was stopped by the addition of 2N sulfuric acid. The color reaction was measured at 490 nm with an automated ELISA plate reader.

The results of this assay showed that monoclonal antibody from hybridomas bound specifically to MAdCAM, and not appreciably to other proteins. The specificity with respect to each of the antibodies was tested in similar experiments where the antibodies were used to block the binding of each other. The results reported indicate that antibodies to six distinct epitopes of human MAdCAM were identified and isolated.

Example 2

Expression of MAdCAM in Inflamed Hepatic Tissues

The following example demonstrates that MAdCAM is expressed in the portal tract vessels of the liver during inflammation but is absent or below the levels of detection in normal liver tissues.

Methods—

Tissues: All tissues, biopsies and surgical resections were fixed in 4% buffered formalin and processed for paraffin embedding. For histological examination, 4 micron sections were cut and stained with haematoxylin and eosin or with rabbit anti-human MAdCAM antibody as described below.

The paraffin sections were deparaffinized in xylene and hydrated in distilled water. Endogenous peroxidase activity was quenched by covering the sections with KPL Blocking Solution (Kirkegaard and Perry Laboratories, Gaithersburg, Md.)(diluted 1:10 in distilled water) for 4 minutes at room temperatures. The sections were then rinsed twice with distilled water for 5 minutes each rinse.

Section were microwaved in Biogenex Citra Solution (Biogenix) for 10 minutes at 99° C., then left at room temperature for 20 minutes. The sections were then rinsed well with distilled water and then with phosphate buffered saline (PBS).

Non-specific antibody binding was blocked by incubation of the sections with 10% goat serum for 20 minutes at room temperature. The sections were then incubated with rabbit anti-human MAdCAM (see Example 1) diluted to 4–7 μg/ml for 30 minutes at room temperature. Control sections were incubated with rabbit isotype control (Zymed, Cat. No. 08 6199). The sections were then rinsed with PBS, twice for 5 minutes each.

Antibody binding was detected by incubating the sections with biotinylated goat anti-rabbit antibody diluted 1:200 in blocking serum for 30 minutes at room temperature, then rinsing with PBS, twice for 5 minutes each. The sections were then incubated with diluted ABC Reagent (Vector Vectastain Elite ABC kit) for 30 minutes at room temperature and rinsed twice with PBS, 5 minutes each time, then incubated with DAB (Pierce) for 5 minutes. The sections were counterstained with Mayer's hematoxylin for 1 minute, followed by a rinse with distilled water.

Lastly, the sections were dehydrated, cleared and mounted in synthetic mounting media.

Results—

While not normally detected in either fetal or adult human liver, MAdCAM is expressed in portal tract vessels in a number of inflammatory liver disorders, including chronic hepatitis C, primary biliary cirrhosis and primary sclerosing cholangitis.

Figure 1A:
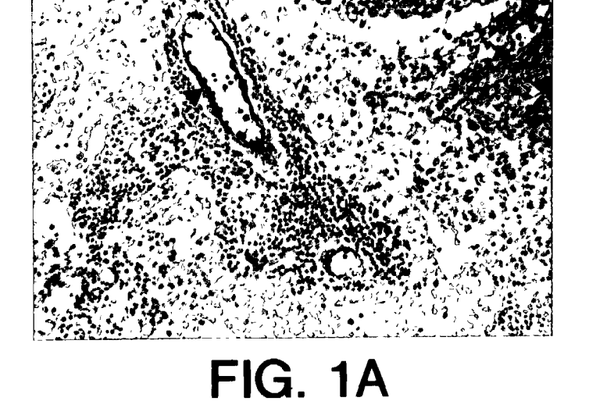
Figure 1B:
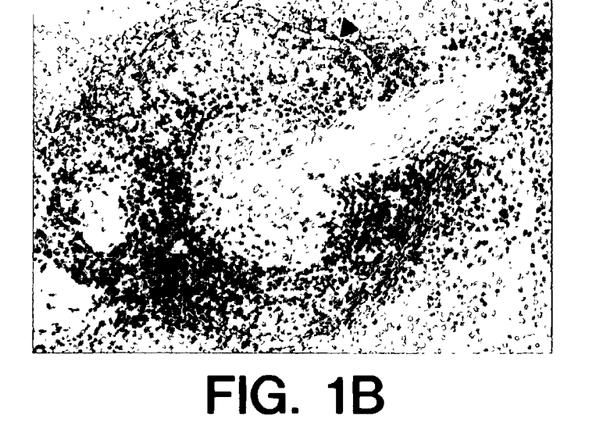
FIG. 1B shows MAdCAM (arrow) expression in normal adult human spleen. Expression was observed on dendritic shaped cells surrounding the splenic white pulp.
Figure 1C:
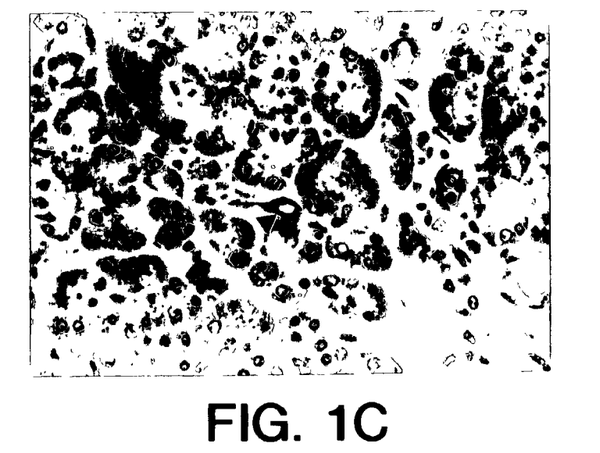
FIG. 1C shows expression of MAdCAM (arrow) on capillary vessels in normal adult human pancreas.

FIG. 1A shows MAdCAM expression on high endothelial venules (arrow) in normal adult human lymph node. FIG. 1B shows MAdCAM expression (arrow) in normal adult human spleen. Expression was observed on dendritic shaped cells surrounding the splenic white pulp. FIG. 1C shows expression of MAdCAM on capillary vessels (arrow) in normal adult human pancreas.

Figure 2A:
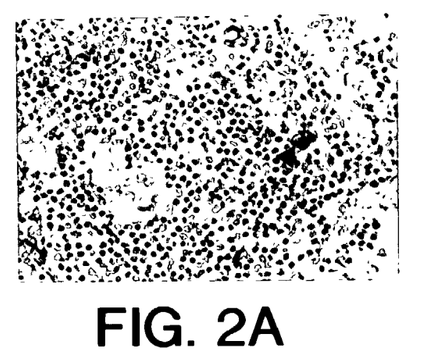
FIG. 2A shows expression of MAdCAM (arrow) on small capillary vessels within inflamed hepatic portal tract.
Figure 2B:
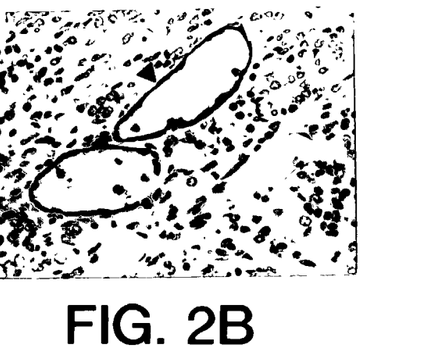
FIG. 2B shows expression of MAdCAM (arrow) on dilated vascular channels within inflamed human hepatic portal tracts.
Figure 2C:
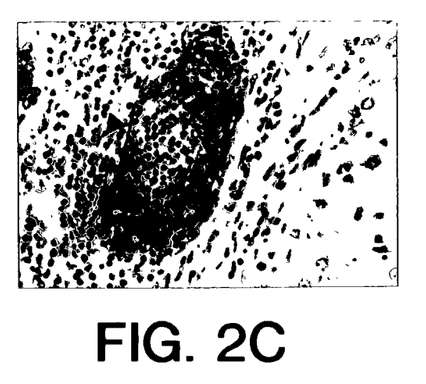
FIG. 2C shows expression of MAdCAM (arrow) on stellate cells surrounding a lymphoid aggregate within a portal tract.
Figure 2D:
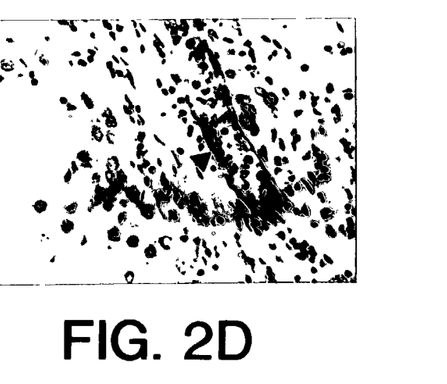
FIG. 2D shows expression of MAdCAM (arrow) on dilated vascular channels within inflamed human hepatic portal tracts.

MAdCAM was detected in portal tract vessels in inflammatory liver disorders. FIG. 2A shows expression of MAd-CAM on small capillary vessels within inflamed hepatic portal tract. FIG. 2B shows expression of MAdCAM on dilated vascular channels within inflamed human hepatic portal tracts. FIG. 2C shows expression of MAdCAM on stellate cells surrounding a lymphoid aggregate within a portal tract. FIG. 2D shows expression of MAdCAM on dilated vascular channels within inflamed human hepatic portal tracts.

Example 3

Identification of Agents Using α4β7/MAdCAM Protein/Protein Assay (1) Isolation of Purified Human α4β7 Integrin Receptors A human 293 kidney cell line transfected with both human α4 and β7 genes at high receptor copy number (>200,000 copies of heterodimeric integrin receptors per cell) was grown and scaled up to 10 liters. Cells were isolated and pelleted. Cell pellet were lysed in 10 volumes of lysis buffer containing 0.5% deoxycholate, 0.5% IGEPAL (NP-40), 50 mM Tris-HCl (pH7.5), 1 mM $Ca^{++}$ $Mg^{++}$ $Mn++$, 10 μg/ml leupeptin, 10 μg/ml aprotinin, and 10 μg/ml pepstatin A. The preparation was homogenized for 30 seconds. The homogenate was centrifuged at 15,000×g for 20 minutes twice. The lysate was filtered through a 0.2 μm filter. The filtrate was loaded onto a rat anti-human β7 antibody affinity column. The bound proteins were eluted with Pierce buffer at pH 6.9 containing 1 mM of $Ca^{++}$, $Mg^{++}$, and $Mn^{++}$ and dialyzed against Tris buffered saline (pH7.2) containing 1 mM $Ca^{++}$, $Mg^{++}$, and $Mn^{++}$.

The dialysate constitutes affinity purified α4β7 integrin receptors.

(2) α4β7/MAdCAM-1 Protein-Protein Assay

The α4β7 integrin receptor preparation at an optimized concentration was immobilized on a solid plastic plate surface precoated with an anti-α4 monoclonal antibody that does not block α4β7 integrin binding to MAdCAM-1. An optimized concentration of MAdCAM-1-Ig-horse radish peroxidase (HRP) conjugate was added for monitoring binding of MAdCAM-1 to α4β7. Inhibitors of the interaction between α4β7 and MAdCAM-1 were added at this time. The bound HRP conjugate is detected with TMB peroxidase substrate (Kirkegaard and Perry Laboratories, Gaithersburg, Md.) spectrophotometrically at an optical density of 450 nm in a microplate reader.

Results

Agents identified in this manner are used in the therapeutic methods disclosed herein.

Example 4

Blocking MAdCAM

JY cells were labeled with 2', 7'-bis-(2-carboxyethyl)-5 (and-6)-carboxyfluoresin (BCECF, Molecular Probes, Eugene, Oreg.) for 30 minutes at 37° C. and resuspended in RPMI 1640 medium with 5 mg/ml BSA. Cells were added to microwells precoated with MAdCAM-1-Ig and incubated for 15 minutes at RT. Unbound cells were washed off and the bound cells were solubilized with 0.1% SDS in 50 mM Tris-HCl (pH 8.5) lysis buffer. The released fluorochrome was monitored by a Cytofluor plate reader (Molecular Devices, Sunnyvale, Calif.) set at 485 nm excitation and 530 nm emission. Maximum fluorescence intensity for the number of input cells was determined and used to calculate the % cell adherence.

Results

Agents identified in this manner are used in the therapeutic methods described herein.

Deposit of Materials

The following cultures are being deposited with the American Type Culture Collection, 10801 University Blvd. Manassas, Va. 20110-2209 USA (ATCC):

| Hybridoma | ATCC No. | Deposit Date |
| --- | --- | --- |
| Mmc3 | CRL-12530 | May 13, 1998 |
| Mmc6 | CRL-12531 | May 13, 1998 |

This deposit is being made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent.

The assignee of the present application agrees that if the cultures on, deposit should die or be lost or destroyed when cultivated under suitable conditions, they will be promptly replaced on notification with a viable specimen of the same culture. Availability of the deposited strains are not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cultures deposited, since the deposited embodiments are intended as an illustration of an aspect of the invention and any cultures that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents.

What is claimed is:

1. A method of treating a hepatic disorder in a subject, comprising administering to the subject an agent that inhibits interaction of MAdCAM with α4β7 integrin, wherein the hepatic disorder is characterized by MAdCAM associated leukocyte recruitment to the liver.

2. The method of claim 1, wherein the hepatic disorder is characterized by inflammation.

3. The method of claim 2, wherein the hepatic disorder is an infection, an autoimmune disorder, an iatrogenic disorder, a hereditary disorder, a cholestatic disorder, sarcoidosis, organ transplant, or graft versus host disease.

4. The method of claim 3, wherein the infection is a viral infection.

5. The method of claim 4, wherein the viral infection is a hepatitis infection.

6. The method of claim 5, wherein the hepatitis infection is a Hepatitis C infection.

7. The method of claim 3, wherein the cholestatic disorder is primary biliary cirrhosis, primary sclerosing cholangitis, or adult idiopathic ductopenia.

8. The method of claim 1, wherein the agent is an antibody or antigen binding fragment thereof.

9. The method of claim 8, wherein the antibody is a monoclonal antibody or an antigen binding fragment thereof.

10. The method of claim 8, wherein the antibody or antigen binding fragment thereof binds to MAdCAM.

11. The method of claim 8, wherein the antibody or antigen binding fragment thereof binds to α4β∂integrin.

12. The method of claim 1, wherein the agent is an immunoadhesin.

13. The method of claim 12, wherein the immunoadhesin comprises a ligand-binding portion of MAdCAM fused to an immunoglobulin constant domain.

14. The method of claim 12, wherein the immunoadhesin comprises a MAdCAM-binding portion of α4β7 integrin fused to an immunoglobulin constant domain.

15. The method of claim 9, wherein the monoclonal antibody is Mmc3 produced from hybridoma cells having ATCC accession number CRL-12530.

16. The method of claim 9, wherein the monoclonal antibody is Mmc6 produced from hybridoma cells having ATCC accession number CRL-12531.

17. A method of inhibiting the binding between a cell expressing a α4β7 integrin and a liver cell expressing MAdCAM, the method comprising contacting one or both of the cells with an agent that inhibits interaction of MAdCAM with α4β7 integrin.

18. The method of claim 17, wherein the contacting occurs in vivo.

19. The method of claim 17, wherein the contacting occurs in vitro.

20. The method of claim 1, wherein the leukocyte is a lymphocyte, macrophage, neutrophil, or eosinophil.

21. The method of claim 1, wherein the agent inhibits leukocyte binding to MAdCAM.

22. The method of claim 2, wherein the inflammation is characterized by hepatic infiltration of leukocytes.

23. The method of claim 22, wherein the leukocytes are lymphocytes.

24. The method of claim 23, wherein the lymphocytes express α4β7 integrin.

25. The method of claim 24, wherein the agent inhibits lymphocyte binding to MAdCAM.

26. The method of claim 1, wherein the hepatic disorder is characterized by expression of MAdCAM in hepatic portal tract.

* * * * *

UNITED STATES PATENT AND TRADEMARK OFFICE
CERTIFICATE OF CORRECTION

PATENT NO. : 7,090,845 B2
APPLICATION NO. : 10/213539
DATED : August 15, 2006
INVENTOR(S) : Fong et al.

Page 1 of 1

It is certified that error appears in the above-identified patent and that said Letters Patent is hereby corrected as shown below:

Column 21
Line 42 "Mn++" should read --$Mn^{++}$--
Line 52 "c4f7" should read --$\alpha 4\beta 7$--

Column 23
Line 55 "$\alpha 4\beta\delta$" should read --$\alpha 4\beta 7$--

Signed and Sealed this

Sixteenth Day of January, 2007

JON W. DUDAS
*Director of the United States Patent and Trademark Office*

SEQUENCE LISTING

<160> NUMBER OF SEQ ID NOS: 2

<210> SEQ ID NO 1
<211> LENGTH: 6
<212> TYPE: PRT
<213> ORGANISM: Homo sapiens

<400> SEQUENCE: 1

Gly Leu Asp Thr Ser Leu
 1               5

<210> SEQ ID NO 2
<211> LENGTH: 5
<212> TYPE: PRT
<213> ORGANISM: Homo sapiens

<400> SEQUENCE: 2

Leu Asp Thr Ser Leu
 1               5